(12) United States Patent
Zheng

(10) Patent No.: US 11,961,611 B2
(45) Date of Patent: Apr. 16, 2024

(54) AUTOMATED BIAS CORRECTION FOR DATABASE SYSTEMS

(71) Applicant: Evernorth Strategic Development, Inc., St. Louis, MO (US)

(72) Inventor: Xiaodong Zheng, Rye Brook, NY (US)

(73) Assignee: Evernorth Strategic Development, Inc., St. Louis, MO (US)

(*) Notice: Subject to any disclaimer, the term of this patent is extended or adjusted under 35 U.S.C. 154(b) by 368 days.

(21) Appl. No.: 17/246,789

(22) Filed: May 3, 2021

(65) Prior Publication Data
US 2022/0351842 A1 Nov. 3, 2022

(51) Int. Cl.
| | |
|---|---|
| *G06N 20/00* | (2019.01) |
| *G06F 40/174* | (2020.01) |
| *G06Q 40/08* | (2012.01) |
| *G16H 10/60* | (2018.01) |
| *G16H 40/20* | (2018.01) |
| *G16H 50/20* | (2018.01) |
| *G16H 50/70* | (2018.01) |

(52) U.S. Cl.
CPC .......... *G16H 40/20* (2018.01); *G06F 40/174* (2020.01); *G06N 20/00* (2019.01); *G06Q 40/08* (2013.01); *G16H 10/60* (2018.01); *G16H 50/20* (2018.01); *G16H 50/70* (2018.01)

(58) Field of Classification Search
CPC ........ G16H 40/20; G16H 10/60; G16H 50/70; G16H 50/20; G06N 20/00; G06F 40/174; G06Q 40/08
See application file for complete search history.

(56) References Cited

U.S. PATENT DOCUMENTS

| | | |
|---|---|---|
| 10,129,367 B2 | 11/2018 | Yan |
| 10,867,308 B2 | 12/2020 | Cui |
| 10,896,742 B2 | 1/2021 | Girshick |

(Continued)

OTHER PUBLICATIONS

Monnat; Shannon M., "Trends in the Family Income Distribution by Race/Ethnicity and Income Source, 1988-2009", Jul. 13, 2015, Population and Development Review, 2012; 51(1): 85-115. (Year: 2015).*

*Primary Examiner* — Kenneth Bartley
*Assistant Examiner* — David Choi
(74) *Attorney, Agent, or Firm* — Harness IP

(57) ABSTRACT

A computer system includes memory hardware and processor hardware configured to execute instructions, including training a machine learning model to generate a claim prediction output, obtaining structured claim data and demographic data specific to a patient entity, processing the structured data to generate the claim prediction output, storing the claim prediction output as a predicted future claim value specific to the patient entity, and assigning the patient entity to a first entity subset or to a second entity subset according to the structured demographic data specific to the patient entity. The instructions also include determining a first proportion of patient entities that have a predicted future claim value exceeding a specified threshold output value, determining an adjusted threshold output value for the second entity subset, and selectively populating schedule entries for the entities having predicted future claim values that exceed a corresponding threshold output value or adjusted threshold output value.

12 Claims, 10 Drawing Sheets

(56) References Cited

U.S. PATENT DOCUMENTS

| | | | |
|---|---|---|---|
| 10,943,676 B2 | 3/2021 | Farooq | |
| 2009/0048877 A1* | 2/2009 | Binns | G06Q 10/04 |
| | | | 705/4 |
| 2011/0295621 A1 | 12/2011 | Farooq | |
| 2012/0197666 A1* | 8/2012 | McDonald Meyer | G06Q 40/08 |
| | | | 705/4 |
| 2016/0162656 A1* | 6/2016 | Di Lascia | G16H 20/10 |
| | | | 705/2 |
| 2016/0203279 A1* | 7/2016 | Srinivas | G16H 10/60 |
| | | | 705/2 |
| 2017/0161772 A1 | 6/2017 | Xiaoxi | |
| 2019/0102802 A1 | 4/2019 | Tuschman | |
| 2019/0172564 A1* | 6/2019 | Chandra | G06N 20/00 |
| 2020/0074874 A1 | 3/2020 | Lathrop | |
| 2020/0219622 A1* | 7/2020 | Zarkoob | G16H 50/20 |
| 2020/0227147 A1 | 7/2020 | Raddatz | |
| 2020/0372338 A1 | 11/2020 | Woods, Jr. | |

* cited by examiner

AUTOMATED BIAS CORRECTION FOR DATABASE SYSTEMS

FIELD

The present disclosure relates to automated bias correction for database systems, such as automatic element adjustment and intervention scheduling.

BACKGROUND

Machine learning models are often used to predict output variables related to database entries, such as healthcare costs, that can be used as proxies of healthcare needs. For example, the output variable could be a predicted future claim cost related to colon cancer treatment, where the machine learning model is trained on historical claim costs for colon cancer treatments. The predicted future colon cancer cost could be used as a proxy to define needs and provision of case management for patients that may be at risk of severe colon cancer complications.

The use of predicted future healthcare cost as a proxy for care provision and needs may cause unintentional bias towards database entries of population subclasses, such as patients that are historically disadvantaged in terms of access to and resources for healthcare. Thus, the historical claim costs may not reflect the need for the healthcare equally among different database entry subclasses.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A computer system includes memory hardware configured to store a machine learning model, historical feature vector inputs, and computer-executable instructions. The historical feature vector inputs include historical claim data structures specific to multiple entities. The system includes processor hardware configured to execute the instructions. The instructions include training the machine learning model with the historical feature vector inputs to generate a claim prediction output, obtaining a set of multiple patient entities, and for each patient entity in the set of multiple patient entities, obtaining structured claim data specific to the patient entity and structured demographic data specific to the patient entity, generating a feature vector input according to the structured claim data, processing, by the machine learning model, the feature vector input to generate the claim prediction output, storing the claim prediction output as a predicted future claim value specific to the patient entity, and assigning the patient entity to a first entity subset or to a second entity subset according to the structured demographic data specific to the patient entity. Patient entities belonging to the first entity subset have at least one demographic characteristic that differs from patient entities belonging to the second entity subset.

The instructions include obtaining a specified threshold output value for entity intervention scheduling or entity case management, determining a first proportion of patient entities within the first entity subset that have a predicted future claim value exceeding the specified threshold output value, and determining an adjusted threshold output value for the second entity subset according to the first proportion, such that a second proportion of patient entities within the second entity subset that have a predicted future claim value exceeding the adjusted threshold output value is equal to the first proportion. For each entity in the first entity subset, the instructions include determining a predicted future claim value of the entity, and in response to the determined value exceeding the specified threshold output value, selectively populating a schedule entry for the entity. For each entity in the second entity subset, the instructions include determining a predicted future claim value of the entity, and in response to the determined value exceeding the adjusted threshold output value, selectively populating a schedule entry for the entity.

In other features, the instructions further include obtaining an event incidence rate for patient entities of the first entity subset, obtaining the event incidence rate for patient entities of the second entity subset, and modifying the adjusted threshold output value according to a ratio of the event incident rates for the first entity subset and the second entity subset. In other features, training the machine learning model includes comparing multiple claim prediction outputs of the machine learning model to historical claim data structures, determining whether an accuracy of the comparison is greater than or equal to a specified accuracy threshold, adjusting parameters of the machine learning model or selecting a different machine learning model type for retraining the machine learning model, in response to a determination that the accuracy of the comparison is less than the specified accuracy threshold, and saving the machine learning model for use in generating claim prediction outputs, in response to a determination that the accuracy of the comparison is greater than or equal to the specified accuracy threshold.

In other features, training the machine learning model includes training multiple machine learning model types simultaneously or in succession, identifying one of the multiple machine learning model types having a highest output accuracy compared to others of the machine learning model types, and saving the identified machine learning model type having the highest output accuracy for use in generating claim prediction outputs. In other features, training the machine learning model includes separating portions of the historical feature vector inputs into structured training data and structured test data, training the machine learning model using the structured training data, testing the trained machine learning model using the structured test data, evaluating results of testing the trained machine learning model, and saving the machine learning model for use in generating claim prediction outputs, in response to a determination that accuracy of the evaluated results is greater than or equal to a specified accuracy threshold.

In other features, training the machine learning model includes at least one of training a neural network machine learning model, training a generalized linear machine learning model, and training a decision tree machine learning model. In other features, selectively populating a schedule entry includes automatically scheduling at least one of a text message intervention, an email intervention, an automated phone call intervention, and a live phone call intervention.

In other features, generating the feature vector input includes generating the feature vector input according to at least one of structured medical history data specific to the patient entity, structured body mass index (BMI) data specific to the patient entity, structured nutrition data specific to the patient entity, the structured demographic data, structured procedure data, structured class data, structured provider data, and structured employer data. In other features, obtaining the specified threshold output value includes obtaining at least one of an entity treatment amount cutoff value and a specified percentage range cutoff value.

In other features, the instructions further include receiving a target demographic group input from a user device, and defining at least the second entity subset according to the target demographic group input. In other features, the instructions further include, for each patient entity in the second entity subset, in response to the determined value exceeding the adjusted threshold output value, selectively transforming a user interface to initiate entity case management for the entity.

A computerized method of automated bias correction for computer systems includes training a machine learning model with historical feature vector inputs to generate a claim prediction output. The historical feature vector inputs include historical claim data structures specific to multiple entities. The method include obtaining a set of multiple patient entities, and for each patient entity in the set of multiple patient entities, obtaining structured claim data specific to the patient entity and structured demographic data specific to the patient entity, generating a feature vector input according to the structured claim data, processing, by the machine learning model, the feature vector input to generate the claim prediction output, storing the claim prediction output as a predicted future claim value specific to the patient entity, and assigning the patient entity to a first entity subset or to a second entity subset according to the structured demographic data specific to the patient entity. Patient entities belonging to the first entity subset have at least one demographic characteristic that differs from patient entities belonging to the second entity subset.

The method includes obtaining a specified threshold output value for entity intervention scheduling or entity case management, determining a first proportion of patient entities within the first entity subset that have a predicted future claim value exceeding the specified threshold output value, and determining an adjusted threshold output value for the second entity subset according to the first proportion, such that a second proportion of patient entities within the second entity subset that have a predicted future claim value exceeding the adjusted threshold output value is equal to the first proportion. For each entity in the first entity subset, the method includes determining a predicted future claim value of the entity, and in response to the determined value exceeding the specified threshold output value, selectively populating a schedule entry for the entity. For each entity in the second entity subset, the method includes determining a predicted future claim value of the entity, and in response to the determined value exceeding the adjusted threshold output value, selectively populating a schedule entry for the entity.

In other features, the method includes obtaining an event incidence rate for patient entities of the first entity subset, obtaining the event incidence rate for patient entities of the second entity subset, and modifying the adjusted threshold output value according to a ratio of the event incident rates for the first entity subset and the second entity subset. In other features, training the machine learning model includes comparing multiple claim prediction outputs of the machine learning model to historical claim data structures, determining whether an accuracy of the comparison is greater than or equal to a specified accuracy threshold, adjusting parameters of the machine learning model or selecting a different machine learning model type for retraining the machine learning model, in response to a determination that the accuracy of the comparison is less than the specified accuracy threshold, and saving the machine learning model for use in generating claim prediction outputs, in response to a determination that the accuracy of the comparison is greater than or equal to the specified accuracy threshold.

In other features, training the machine learning model includes training multiple machine learning model types simultaneously or in succession, identifying one of the multiple machine learning model types having a highest output accuracy compared to others of the machine learning model types, and saving the identified machine learning model type having the highest output accuracy for use in generating claim prediction outputs. In other features, training the machine learning model includes separating portions of the historical feature vector inputs into structured training data and structured test data, training the machine learning model using the structured training data, testing the trained machine learning model using the structured test data, evaluating results of testing the trained machine learning model, and saving the machine learning model for use in generating claim prediction outputs, in response to a determination that accuracy of the evaluated results is greater than or equal to a specified accuracy threshold.

In other features, selectively populating a schedule entry includes automatically scheduling at least one of a text message intervention, an email intervention, an automated phone call intervention, and a live phone call intervention. In other features, generating the feature vector input includes generating the feature vector input according to at least one of structured medical history data specific to the patient entity, structured body mass index (BMI) data specific to the patient entity, structured nutrition data specific to the patient entity, the structured demographic data, structured procedure data, structured class data, structured provider data, and structured employer data.

In other features, obtaining the specified threshold output value includes obtaining at least one of an entity treatment amount cutoff value and a specified percentage range cutoff value. In other features, the method includes receiving a target demographic group input from a user device, and defining at least the second entity subset according to the target demographic group input.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

In the drawings, reference numbers may be reused to identify similar and/or identical elements.

DETAILED DESCRIPTION

High-Volume Pharmacy

Figure 1:
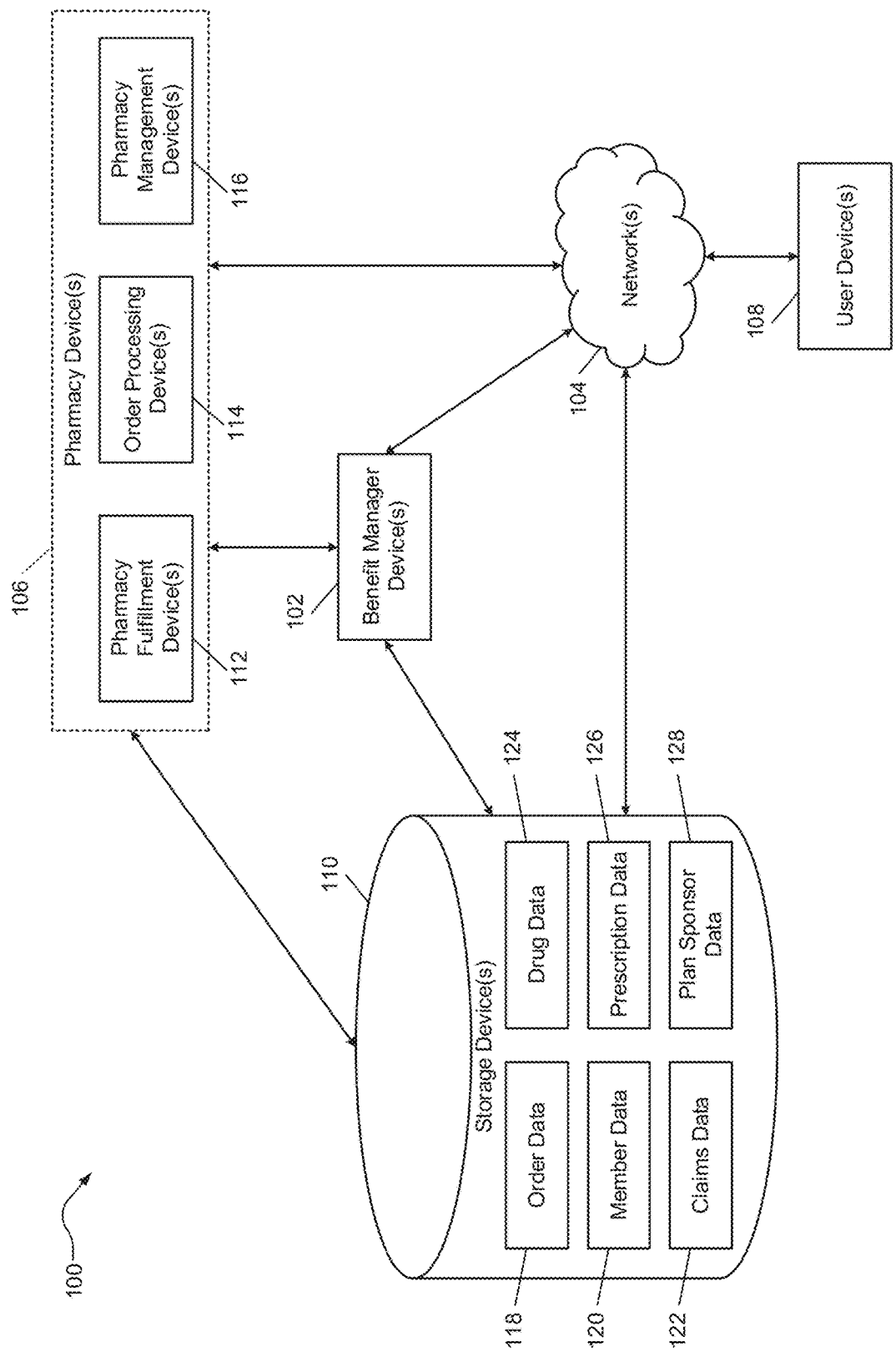
FIG. 1 is a functional block diagram of an example system including a high-volume pharmacy.

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104.

The system 100 may also include one or more user device(s) 108. A user, such as a pharmacist, patient, data analyst, health plan administrator, etc., may access the benefit manager device 102 or the pharmacy device 106 using the user device 108. The user device 108 may be a desktop computer, a laptop computer, a tablet, a smartphone, etc.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in a storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Virginia.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfillment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
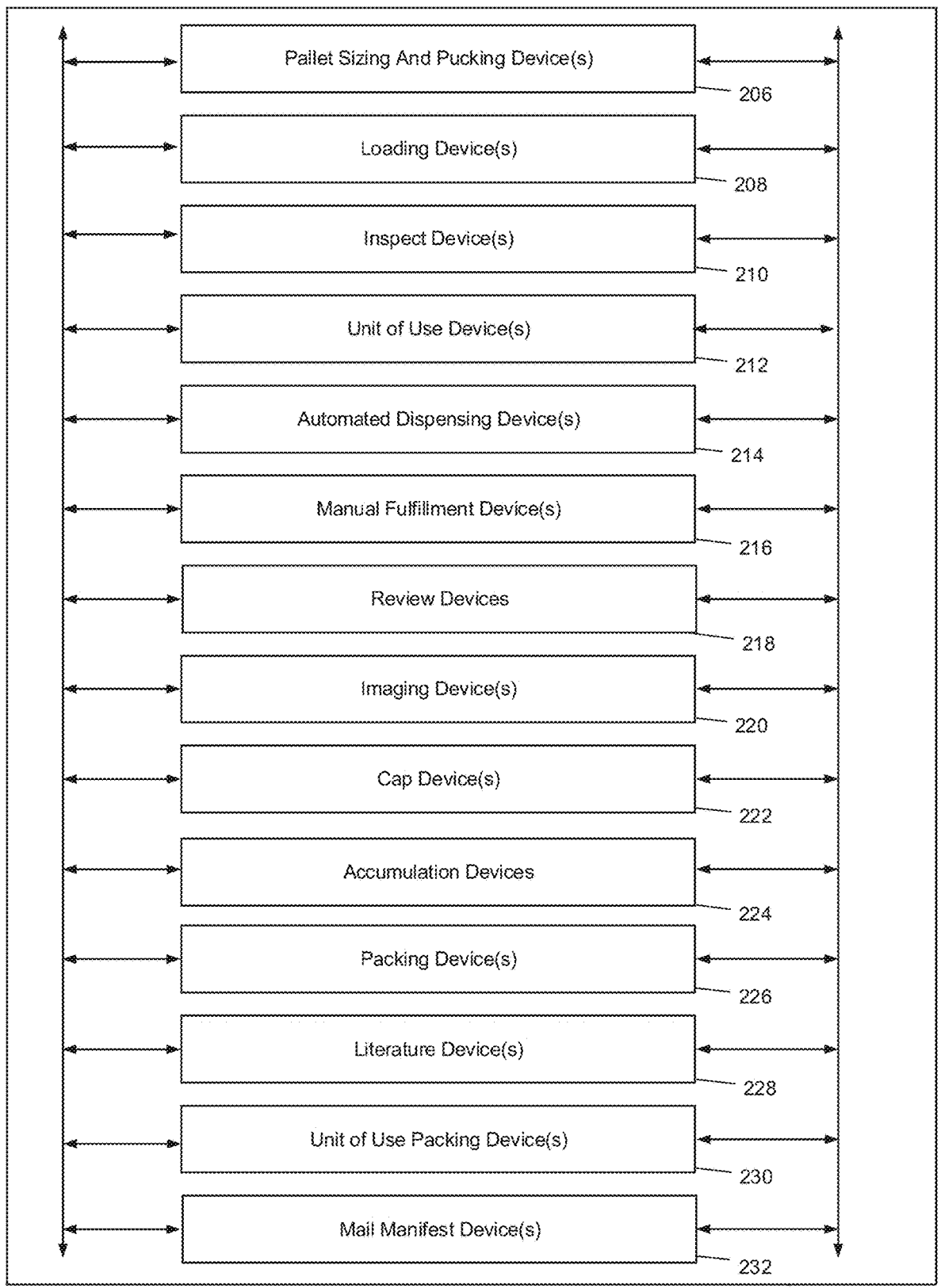
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
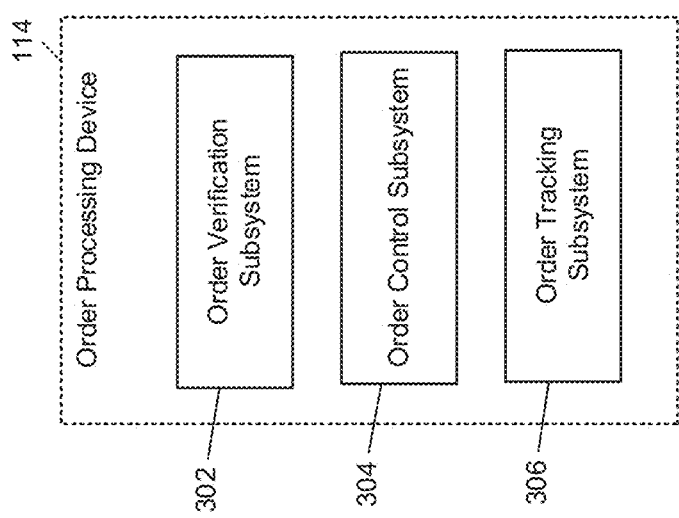
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Database System Automated Bias Correction

Figure 4:
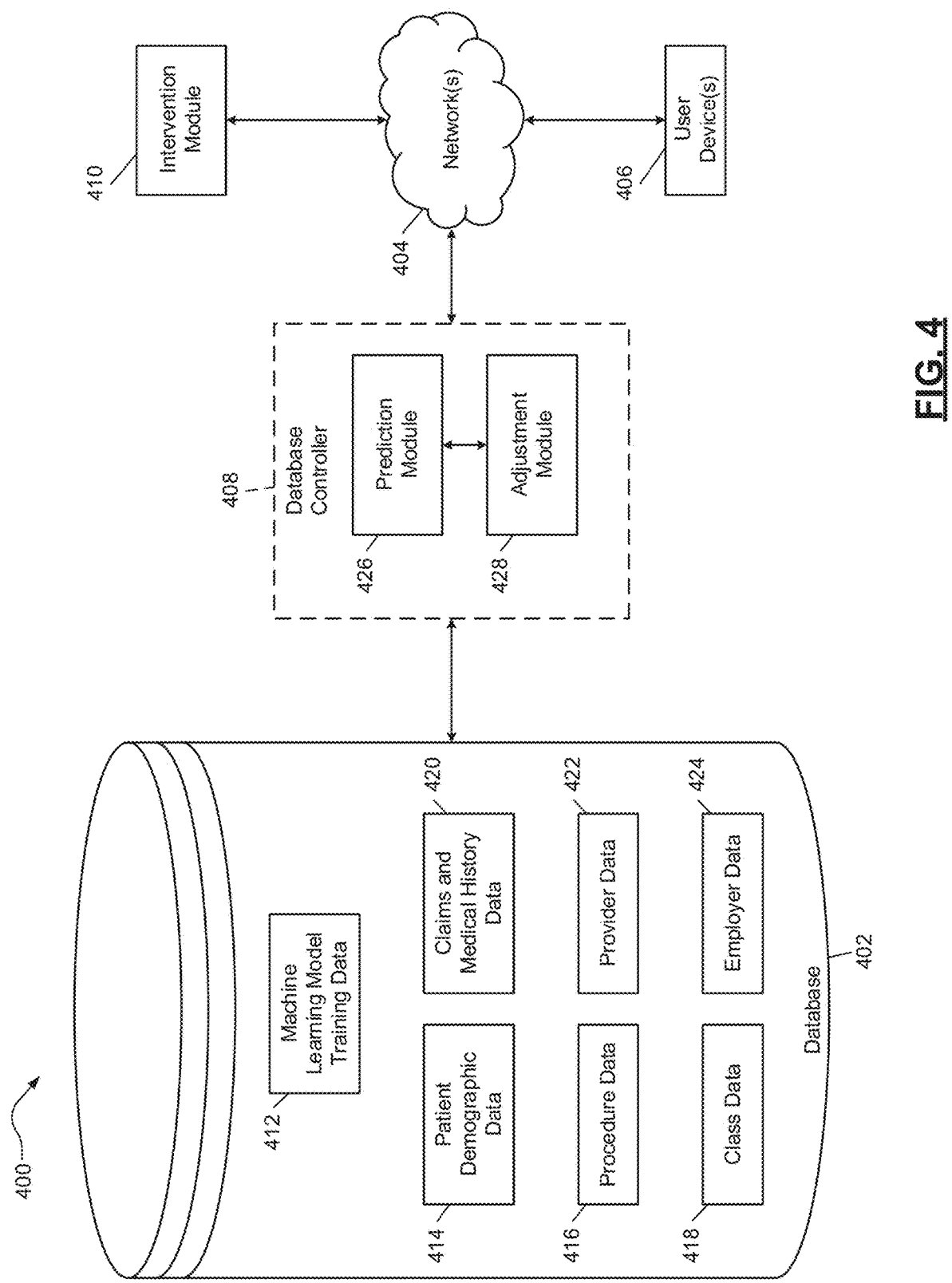
FIG. 4 is a functional block diagram of a system for automated bias correction for database systems.

FIG. 4 is a functional block diagram of an example system 400 for automated bias correction for database systems, which includes a database 402. While the system 400 is generally described as being deployed in a computer network system, the database 402 and/or components of the system 400 may otherwise be deployed (for example, as a standalone computer setup). The system 400 may include a desktop computer, a laptop computer, a tablet, a smartphone, etc.

As shown in FIG. 4, the database 402 stores machine learning model training data 412, patient demographic data 414, procedure data 416, class data 418, claims and medical history data 420, provider data 422 and employer data 424. FIG. 4 illustrates example elements of the machine learning model training data 412, patient demographic data 414, procedure data 416, class data 418, claims and medical history data 420, provider data 422 and employer data 424. In various implementations, the database 402 may store other types of data as well.

The machine learning model training data 412, patient demographic data 414, procedure data 416, class data 418, claims and medical history data 420, provider data 422 and employer data 424 may be located in different physical memories within the database 402, such as different random access memory (RAM), read-only memory (ROM), a non-volatile hard disk or flash memory, etc. In some implementations, the machine learning model training data 412, patient demographic data 414, procedure data 416, class data 418, claims and medical history data 420, provider data 422 and employer data 424 may be located in the same memory (such as in different address ranges of the same memory). In various implementations the machine learning model training data 412, patient demographic data 414, procedure data 416, class data 418, claims and medical history data 420, provider data 422 and employer data 424, may each be stored as structured data in any suitable type of data store.

The machine learning model training data 412 may include any suitable data for training one or more machine learning models, such as historical claim data structures related to one or more of the patient demographic data 414, procedure data 416, class data 418, claims and medical history data 420, provider data 422 and employer data 424. The machine learning model training data 412 may include historical feature vector inputs that are used to train one or more machine learning models to generate a claim prediction output, such as a prediction of future healthcare costs for patients within a population of database entries.

In various implementations, users may run the machine learning model via the user device 406, to identify patients having a highest predicted health risk based on future expected healthcare costs, in order to schedule interventions or other case management for patients having the highest needs. The user device 406 may include any suitable user device for displaying text and receiving input from a user, including a desktop computer, a laptop computer, a tablet, a smartphone, etc. The user device 406 may access the database 402 directly, or may access the database 402 through one or more networks 404 and the database controller 408. Example networks may include a wireless network, a local area network (LAN), the Internet, a cellular network, etc.

The database controller 408 may include one or more modules for automated bias correction of database entries. For example, FIG. 4 illustrates a prediction module 426 and an adjustment module 428. The prediction module 426 may include one or more machine learning models, which may be trained based on the machine learning model training data 412. The prediction module 426 may use one or more of the patient demographic data 414, procedure data 416, class data 418, claims and medical history data 420, provider data 422, and employer data 424, to predict future healthcare costs for patients within a population of entries of the database 402.

As shown in FIG. 4, the database controller 408 may communicate with an intervention module 410 via the network(s) 404. For example, the output from the prediction module 426 may be used to schedule interventions for high risk patients (such as those predicted to have the highest future healthcare costs), in an attempt to reduce potential future health events for those patients. Example interventions include, but are not limited to, sending text messages about suggested care, sending emails, automated phone calls, and live physician or pharmacist phone calls.

The database controller 408 also includes an adjustment module 428. The adjustment module 428 may be used for automated bias correction for the prediction module 426, as explained further below. For example, outputs of the prediction module 426 may be biased towards subclasses of the patient population having increased access and resources for healthcare, leading to higher predicted future healthcare costs and higher likelihoods of interventions and other case management for those subclasses. The adjustment module 428 may automatically correct biases of the prediction module 426 to balance representation of different subclasses of database entries of the patient population by adjusting thresholds for subclasses that, for example, have reduced access and resources for healthcare.

Referring back to the database 402, the patient demographic data 414 may include any suitable demographic data patient such as a patient's age, race, and sex. The procedure data 416 may include any suitable data about different healthcare procedures, including typical costs of the procedures, such as colon cancer treatments, other cancer treatments, diabetes treatments, heart disease treatments, etc. The class data 418 may include data relating to different subclasses of the patient population, such as different age groups within the population, different race groups of the population, different sex subclasses of the population, etc. The class data 418 may be used to identify minority groups, lower socioeconomic groups, patient groups that are underrepresented in access to health care, etc. The adjustment module 428 may be used to correct biases against these groups when factors such as predicted health care costs are used to identify high-risk individuals for interventions or other case management.

The claims and medical history data 420 may include any suitable data about past claims of patients or past medical history of patients, such as a body mass index (BMI) of the patient or nutrition data for the patient. This data may be used by the prediction module 426 to predict future expected healthcare costs for patients. The provider data 422 may include any suitable data about healthcare providers, such as expected costs for different treatments for patients of the providers. The employer data 424 may include any suitable data related to employers of patients, such as healthcare plans and coverages offered to patients employed by the employer. As mentioned above, in various implementations more or less (or other) data may be stored in the database 402.

Figure 5:
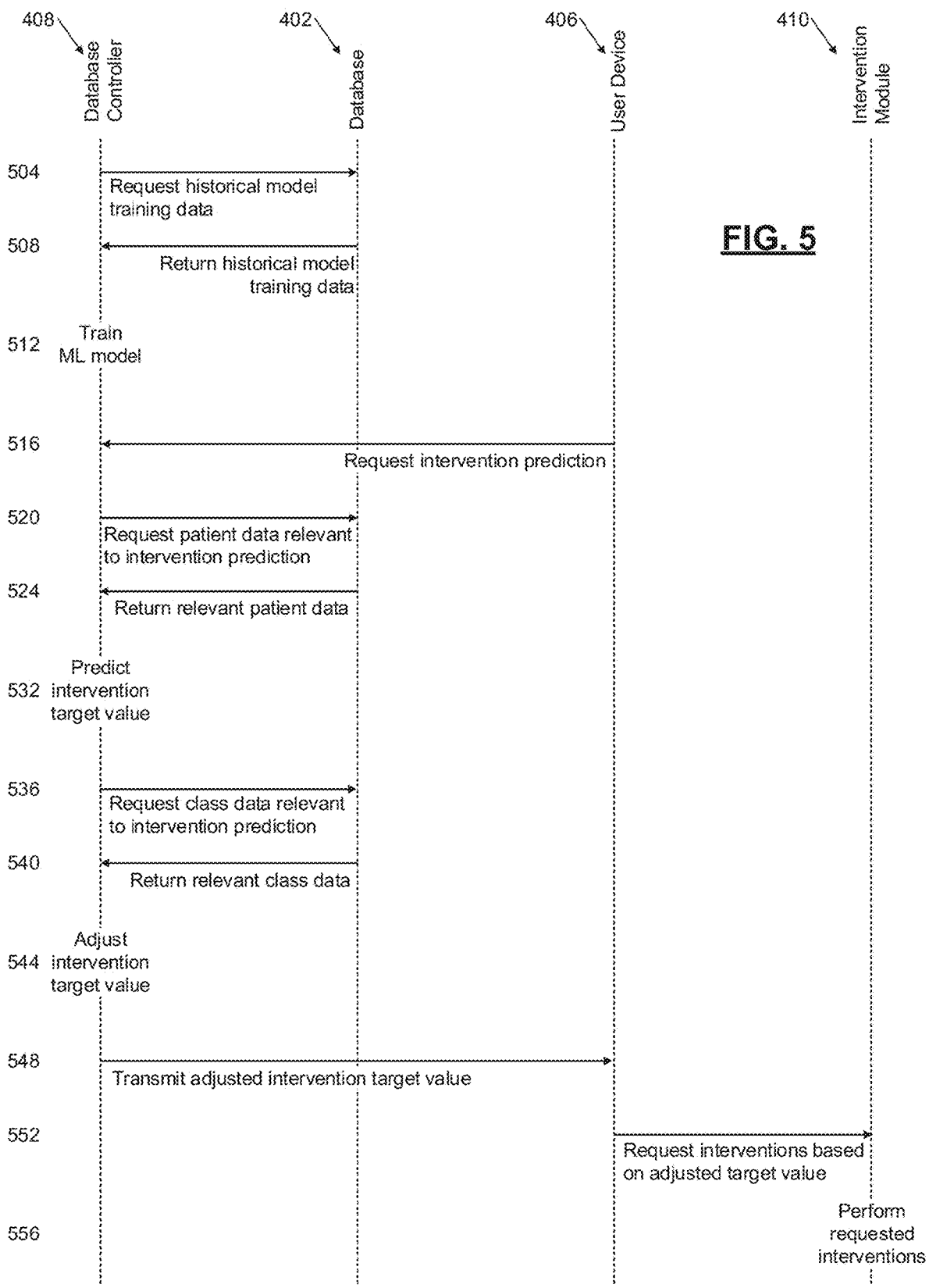
FIG. 5 is a message sequence chart illustrating example interactions between elements of the system of FIG. 4.

FIG. 5 is a message sequence chart illustrating example interactions between the database controller 408, the database 402, the user device 406, and the intervention module 410, during automated bias correction of database entries of the system 400. As shown in FIG. 5, the database controller 408 requests historical claims data, such as the machine learning model training data 412, at line 504. At line 508, the database 402 returns historical model training data to the database controller 408. The database controller 408 then trains the machine learning model using the historical model training data at line 512.

At line 516, the user device 406 requests an intervention prediction. For example, a user may request a prediction of future colon cancer costs for a population of patients, via the user device 406, to schedule interventions or other case management for the highest risk patients. At line 520, the database controller 408 requests patient data relevant to the intervention prediction. The database 402 returns the relevant patient data to the database controller 408, at line 524. The database controller 408 then predicts an intervention target value at line 532. For example, the database controller 408 may use the prediction module 426 to determine which patients have expected costs above a target value threshold, such as the highest risk patients that have expected future colon cancer costs above $30,000.

The database controller 408 requests class data relevant to the intervention prediction, at line 536. At line 540, the database 402 returns relevant class data to the database controller 408. The database controller 408 then adjusts the intervention target value based on the class data, at line 544. For example, and as explained further below, the adjustment module 428 may identify subclasses of the patient population having different average costs for colon cancer treatments. The adjustment module 428 may then adjust the target value for identified subclasses, such as lowering the target value for identified subclasses with lower average treatment costs, or to correct any potential bias against the identified subclasses. For example, if a subclass of black patients has an average colon cancer treatment expenditure that is only 80% of the average expenditure for a subclass of white patients, the target value may be reduced by a certain percentage (for example, as determined by the method of FIG. 8 described further below) for the subclass of black patients, to avoid a bias against that subclass that could result in subclass not receiving any scheduled interventions or other case management.

At line 548, the database controller 408 transmits the adjusted intervention target value to the user device 406. The user device 406 then requests interventions based on adjusted target value, at line 552. At line 556, the intervention module 410 performs the requested interventions. As mentioned above, the intervention module 410 may send a text message to the patient, send an email to the patient, schedule an automated telephone call to the patient, a arrange a live call from a physician or pharmacist, etc.

Machine Learning Model

Figure 6:
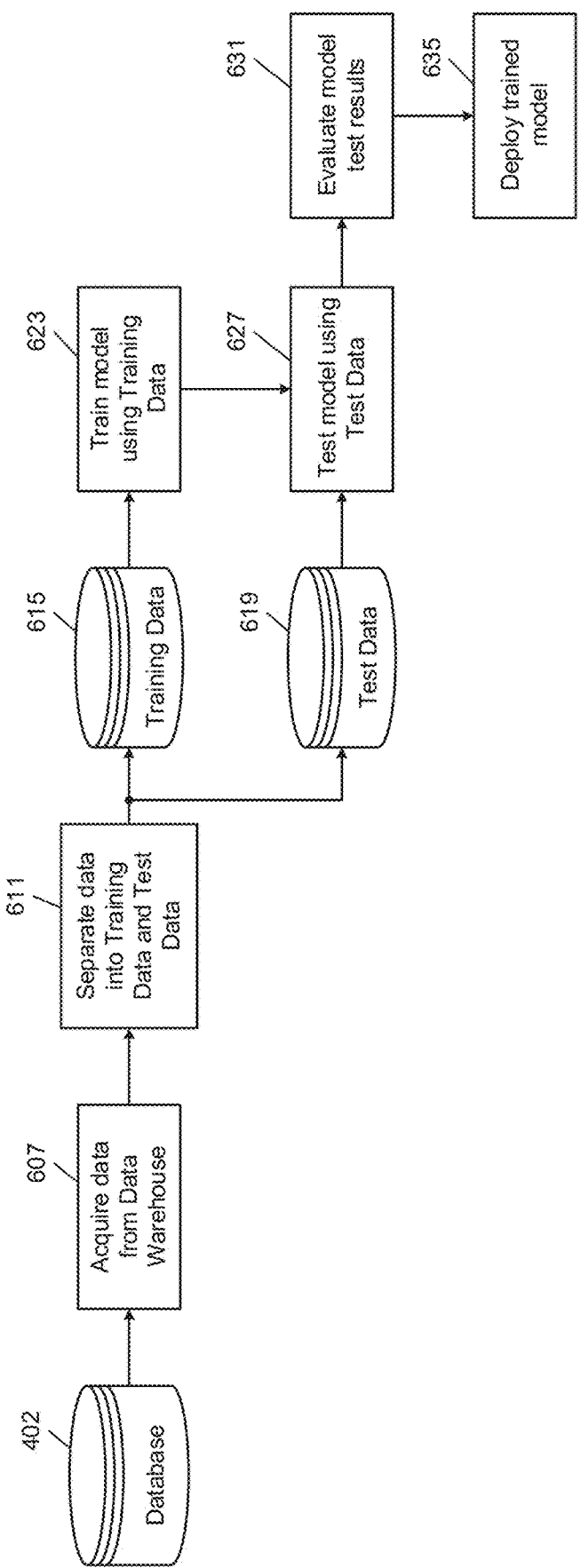
FIG. 6 is a flowchart illustrating an example process for training a machine learning model.

FIG. 6 illustrates an example process for generating a machine learning model (for example, using the prediction module 426 of FIG. 4). At 607, control obtains data from a data warehouse, such as the database 402. The data may include any suitable data for developing the machine learning model. For example, the machine learning model training data 412 from the database 402 may be used to generate historical feature vector inputs for training the machine learning model. The historical feature vector inputs may include, for example, one or more of the patient demographic data 414, procedure data 416, class data 418, claims and medical history data 420, provider data 422, and employer data 424, of the database 402 in FIG. 4.

At 611, control separates the data obtained from the database 402 into training data 615 and test data 619. The training data 615 is used to train the model at 623, and the test data 619 is used to test the model at 627. Typically, the set of training data 615 is selected to be larger than the set of test data 619, depending on the desired model development parameters. For example, the training data 615 may include about seventy percent of the data acquired from the database 402, about eighty percent of the data, about ninety percent, etc. The remaining thirty percent, twenty percent, or ten percent, is then used as the test data 619.

Separating a portion of the acquired data as test data 619 allows for testing of the trained model against actual historical output data, to facilitate more accurate training and development of the model at 623 and 627. The model may be trained at 623 using any suitable machine learning model techniques, including those described herein, such as random forest, generalized linear models, decision tree, and neural networks.

At 631, control evaluates the model test results. For example, the trained model may be tested at 627 using the test data 619, and the results of the output data from the tested model may be compared to actual historical outputs of the test data 619, to determine a level of accuracy. The model results may be evaluated using any suitable machine learning model analysis, such as the example techniques described further below.

After evaluating the model test results at 631, the model may be deployed at 635 if the model test results are satisfactory. Deploying the model may include using the model to make predictions for a large-scale input dataset with unknown outputs, and using the model to schedule interventions or other case management for high risk patients identified by the model. If the evaluation of the model test results at 631 is unsatisfactory, the model may be developed further using different parameters, using different modeling techniques, using other model types, etc.

Figure 7A:
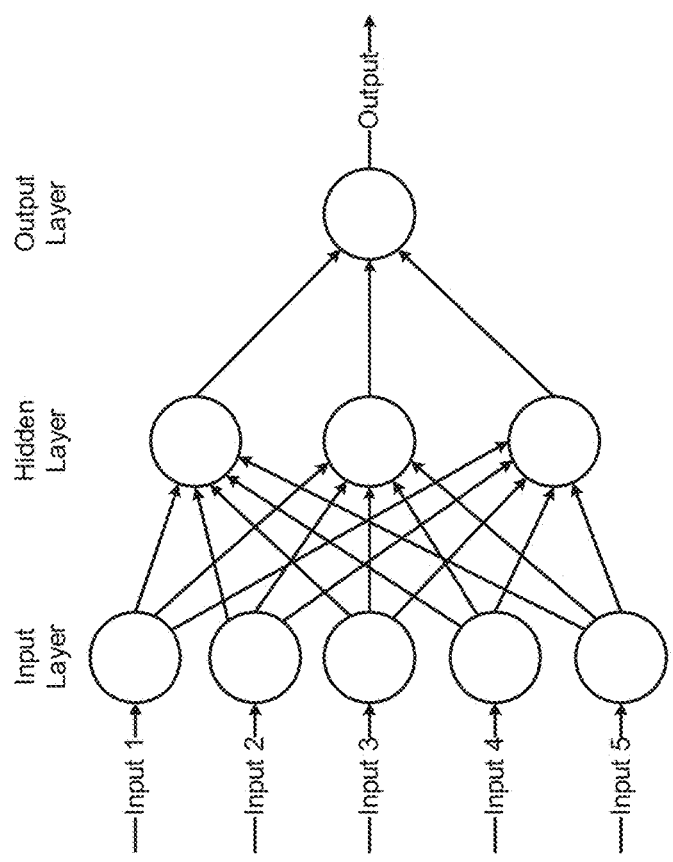
FIG. 7A is graphical representation of layers of an example neural network machine learning model.
Figure 7B:
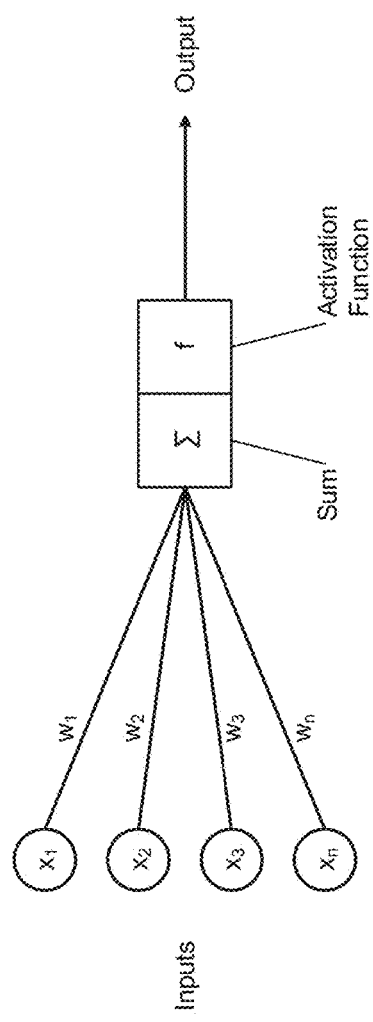
FIG. 7B is a graphical representation of inputs to an example activation function of the machine learning model of FIG. 7A.

FIGS. 7A and 7B show an example of a recurrent neural network used to generate models such as those described above with reference to FIG. 6, using machine learning techniques. Machine learning is a method used to devise complex models and algorithms that lend themselves to prediction (for example, future healthcare cost prediction). The models generated using machine learning, such as those described above with reference to FIG. 6, can produce reliable, repeatable decisions and results, and uncover hidden insights through learning from historical relationships and trends in the data.

The purpose of using the recurrent neural-network-based model, and training the model using machine learning as described above with reference to FIG. 6, may be to directly predict dependent variables without casting relationships between the variables into mathematical form. The neural network model includes a large number of virtual neurons operating in parallel and arranged in layers. The first layer is the input layer and receives raw input data. Each successive layer modifies outputs from a preceding layer and sends them to a next layer. The last layer is the output layer and produces output of the system.

FIG. 7A shows a fully connected neural network, where each neuron in a given layer is connected to each neuron in a next layer. In the input layer, each input node is associated with a numerical value, which can be any real number. In each layer, each connection that departs from an input node has a weight associated with it, which can also be any real number (see FIG. 7B). In the input layer, the number of neurons equals number of features (columns) in a dataset. The output layer may have multiple continuous outputs.

The layers between the input and output layers are hidden layers. The number of hidden layers can be one or more (one hidden layer may be sufficient for most applications). A neural network with no hidden layers can represent linear separable functions or decisions. A neural network with one hidden layer can perform continuous mapping from one finite space to another. A neural network with two hidden layers can approximate any smooth mapping to any accuracy.

The number of neurons can be optimized. At the beginning of training, a network configuration is more likely to have excess nodes. Some of the nodes may be removed from the network during training that would not noticeably affect network performance. For example, nodes with weights approaching zero after training can be removed (this process is called pruning). The number of neurons can cause underfitting (inability to adequately capture signals in dataset) or over-fitting (insufficient information to train all neurons; network performs well on training dataset but not on test dataset).

Various methods and criteria can be used to measure performance of a neural network model (such as for the model test result evaluation at 631 in FIG. 6). For example, root mean squared error (RMSE) measures the average distance between observed values and model predictions. Coefficient of Determination ($R^2$) measures correlation (not accuracy) between observed and predicted outcomes (for example, between trained model outputs and actual outputs of the test data 619, etc.). This method may not be reliable if the data has a large variance. Other performance measures include irreducible noise, model bias, and model variance. A high model bias for a model indicates that the model is not able to capture true relationship between predictors and the outcome. Model variance may indicate whether a model is not stable (a slight perturbation in the data will significantly change the model fit).

Automated Bias Correction Process

Figure 8:
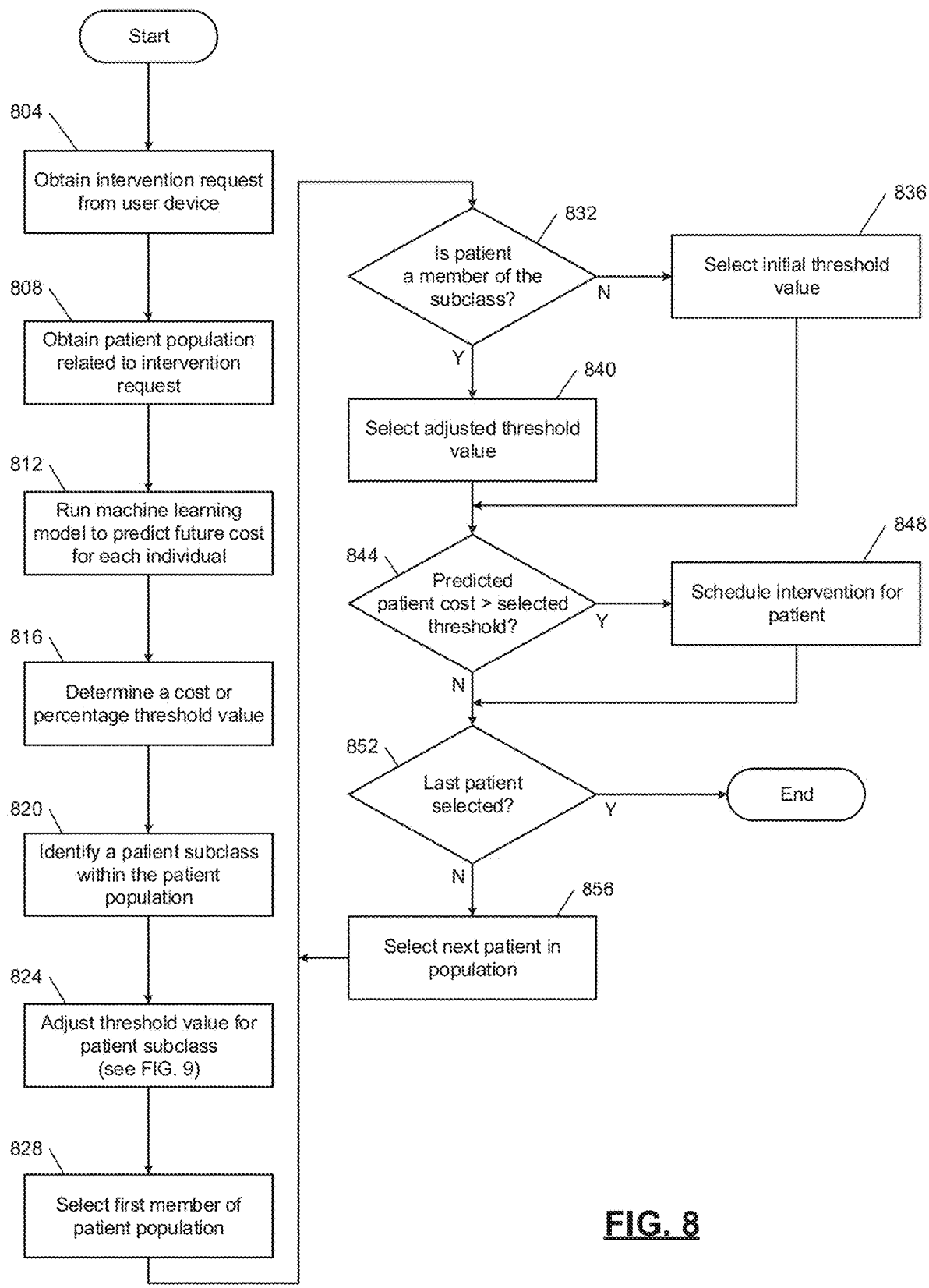
FIG. 8 is a flowchart depicting an example process for automatically correcting bias of database entries.

FIG. 8 is a flowchart depicting an example process for automatically correcting bias of database entries. In various implementations, the example process may be performed by modules of the database controller 408, including the prediction module 426 and the adjustment module 428. At 804, control begins by obtaining an intervention request from the user device 406. For example, a user may request prediction of expected future healthcare costs for a particular treatment such as colon cancer treatments, for patients in a population.

At 808, control obtains a patient population related to the intervention request, such as all patients in a health care plan, all patients associated with a specific employer, all patients in a particular treatment plan, etc. At 812, control runs the machine learning model to predict future health care costs for each individual. For example, control may supply feature vector inputs to the prediction module 426 to predict the future healthcare costs. At 816, control determines a cost or percentage threshold value. For example, control may determine to identify patients having greater than $30,000 of predicted future healthcare costs, patients having greater than $100,000 of predicted future healthcare costs, etc. Control may identify a top 1% of highest predicted cost patients, a top 5%, a top 10%, or any other suitable threshold value.

Figure 9:
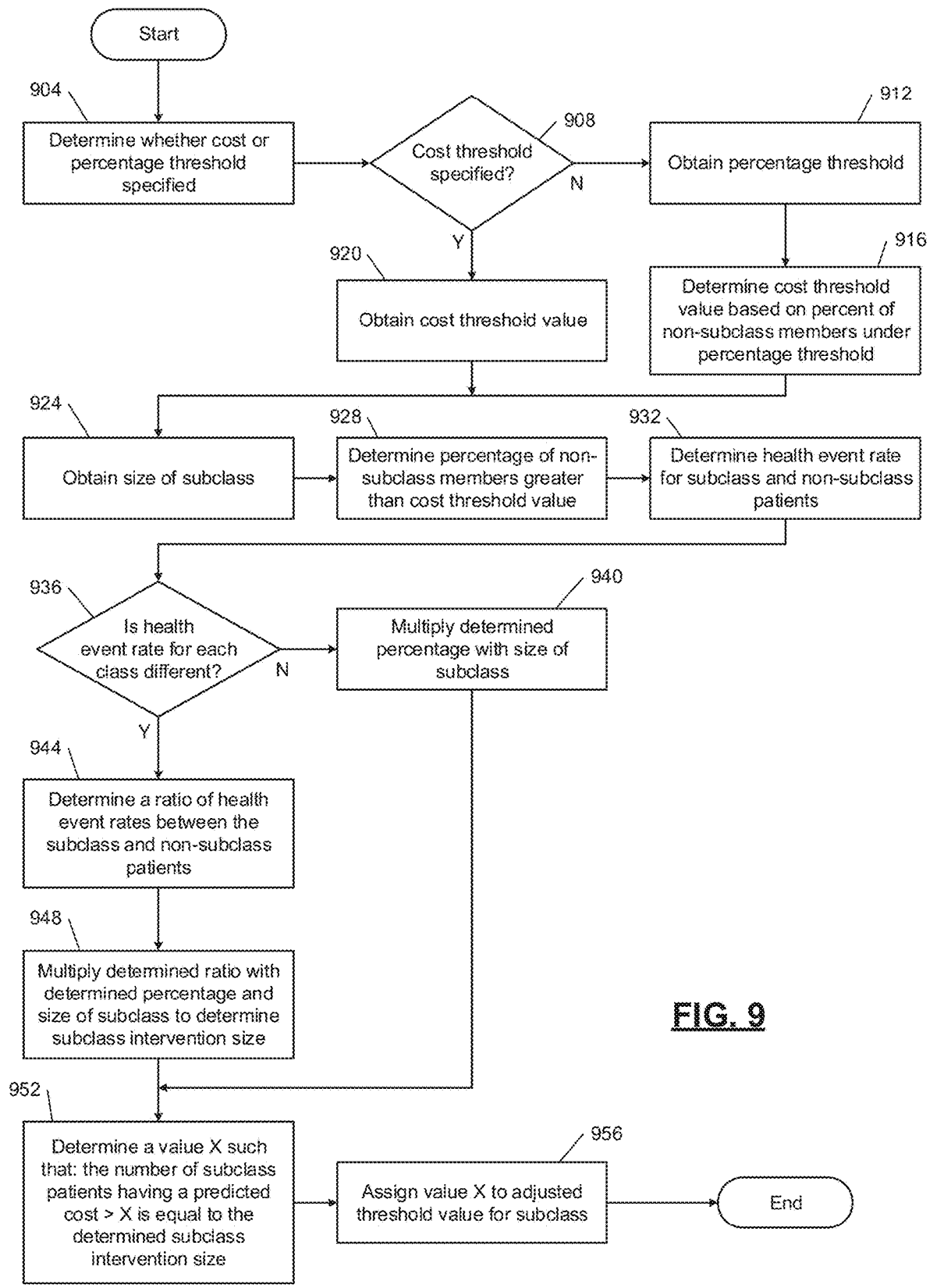
FIG. 9 is a flowchart depicting an example process for adjusting a threshold for an identified subclass of database entries to correct potential bias towards the identified subclass.

Control then identifies a patient subclass within the patient population at 820. For example, control may identify a minority subclass of patients, a subclass that is underrepresented or has less access to healthcare, etc. The subclass may be specified by the user, or may be determined by control according to predefined subclasses. At 824, control adjusts threshold values for the patient subclass. The threshold adjustment may be performed by the adjustment module 428 of the database controller 408, and an example adjustment process is illustrated in FIG. 9 and described further below. For example, the cost or percentage thresholds may be reduced for the identified subclass to correct bias, if an average treatment expenditure for the identified subclass is less than an average treatment expenditure for other subclasses, or if the identified subclass has a higher incidence rate of specific treatments compared to other subclasses. The average treatment expenditure may be determined based on claims or other payment data. The incidence rate may be determined based on medical research studies, provider data, etc.

At 828, control selects a first member of a patient population. Control then determines whether the patient is a member of the identified subclass at 832. If not, control selects the initially determined threshold value at 836 (for example, the cost or percentage threshold value determined at 816). If control determines that the patient is a member of the identified subclass, control selects the adjusted threshold value at 840. For example, if control determines that the patient belongs to a minority group, control may select the adjusted threshold value from 824 to correct potential bias towards the patient's minority group.

Control determines whether the predicted patient cost is greater than the selected threshold at 844. For example, control may compare the predicted healthcare cost for the patient from the prediction module 426 to the adjusted threshold if the patient belongs to the identified subclass, or compare the predicted cost to the initially specified threshold if the patient does not belong to the identified subclass, in order to determine whether the patient's predicted future healthcare cost exceeds the corresponding threshold. If so, control schedules an intervention request for the patient at 848, which may include at least one of a text message, an email, an automated phone call, a live call from a pharmacist or physician, enrollment in a specified care management plan, etc.

After scheduling the intervention request at 848, or if control determines at 844 that the patient's predicted cost does not exceed the threshold, control proceeds to 852 to determine whether the last patient has been selected. If so, control ends the process. If not, control selects the next patient in the population at 856 and returns to 832 to determine whether the patient is a member of the identified subclass.

FIG. 9 is a flowchart depicting an example process for adjusting a threshold for an identified subclass of database entries to correct potential bias towards the identified subclass. At 904, control begins by determining whether a cost or percentage threshold has been applied. As mentioned above, a threshold could be specified as a target value of future predicted healthcare costs to identify high risk individuals, or a top percentage of highest future predicted healthcare cost individuals could be selected.

At 908, control determines whether a cost threshold has been specified. If so, control obtains the cost threshold value at 920. If not, control obtains the percentage threshold at 912, and then determines a cost threshold value at 916 based on a percentage of non-subclass members under the percentage threshold. For example, if a percentage threshold value of 5% is used, control may determine a predicted cost value that is exceeded by 5% of patients that do not belong to the identified subclass. Control then obtains a size of the subclass at 924.

Control optionally proceeds to 928 to determine a percentage of non-subclass member that are greater than the cost threshold value. For example, if the identified cost threshold value is $30,000, control may determine that 10% of patients that are not in the identified subclass have predicted future healthcare costs over $30,000. This step may be omitted if a percentage threshold is specified initially instated of a cost threshold, because control could use the specified percentage threshold at this stage.

At 932, control determines a health event rate for patients of the subclass and for patients that are not part of the subclass. For example, research articles may be analyzed to determine that a minority group has a rate of colon cancer that is double the rate of patients that are not in the minority group (which may be due to less frequent testing, detection and prevention of colon cancer for the minority group). At 936, control determines whether the health event rate for each class is different. If not, control multiples the determined percentage from 928 (or the percentage specified at 912) with the size of the subclass at 940. This result indicates a number of patients in the subclass that should be targeted for intervention in order to correct bias in the prediction model.

If control determines at 936 that the health event rate is different for each class, control determines a ratio of health event rates between the subclass and the non-subclass patients at 944 (such as the subclass patients having double the event rate of the non-subclass patients). Control then multiplies the determined ratio with the determined percentage and size of subclass at 948, in order to determine the subclass intervention size.

At 952, control determines a value of X such that the number of patients in the subclass having a predicted cost greater than X is equal to the determined subclass intervention size. Control then assigns the value X to the adjusted threshold value for the subclass at 956.

Figure 10:
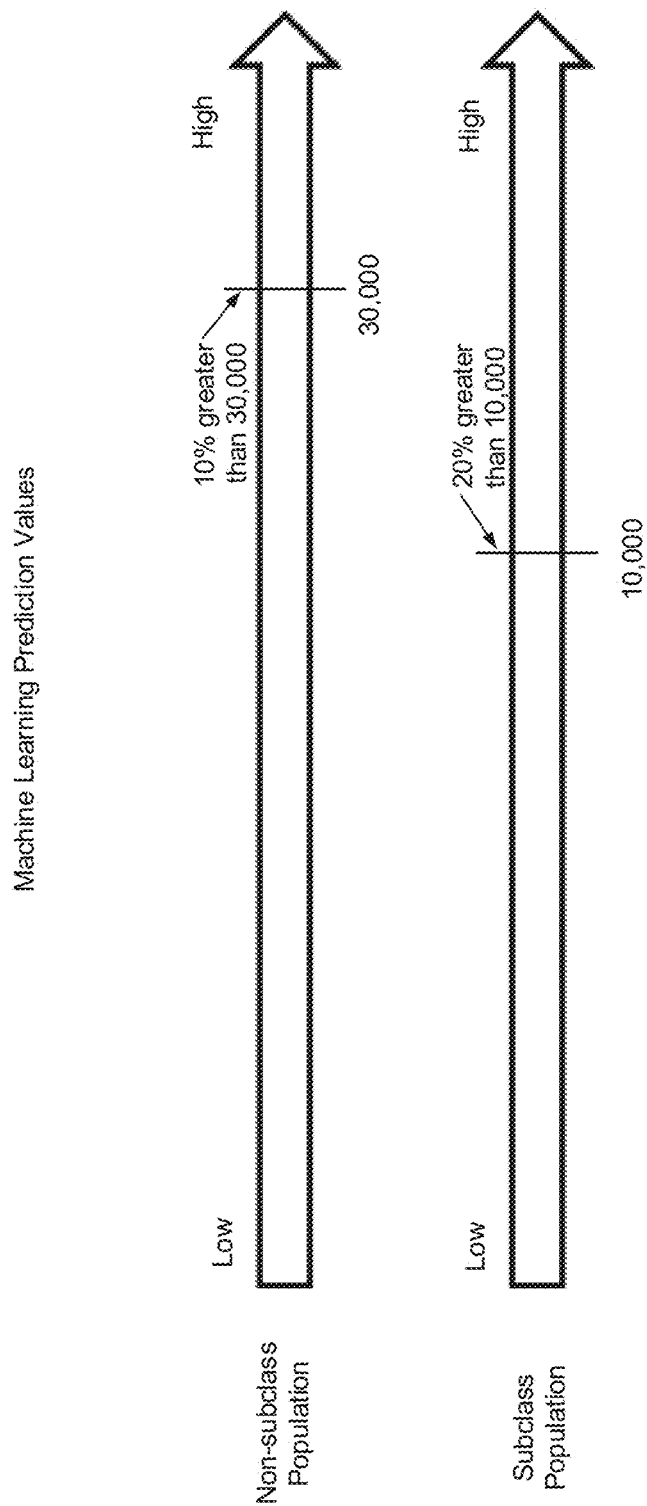
FIG. 10 is a graphical representation of an example adjusted threshold value to correct bias for database entries belonging to an identified subclass.

FIG. 10 is a graphical representation of an example adjusted threshold value to correct bias for database entries belonging to an identified subclass. In this example, the method may automatically correct for potential bias of the machine learning model of the prediction module 426, due to the model being trained on historical costs data where different classes of patients have different levels of average treatment expenditures.

As one example, the output variable may be colon cancer cost, and research may indicate that black patients are about twice as likely as white patients to have colon cancer in the United States. If a high risk segment is defined as those patients having a predicted cost greater than $30,000, such a threshold may potentially qualify white patients more than black patients even if the need for care is greater among the black patient subclass. One example reason is that historically the treatment expenditure for black patients tends to be less on average than the colon cancer treatment expenditure for white patients.

In the example of FIG. 10, the automated bias correction method looks at distributions of predicted costs separately for black patient subclasses and white patient subclasses, and makes automated adjustments to the threshold values for each subclass so the qualification requirements for intervention or other case management are not biased against members of the black patient subclass. For example, if 10% of the white patient subclass is predicted to have future colon cancer treatment costs greater than $30,000, the automated bias correction method may revise the cutoff for black patients from $30,000 to a value of $X, such that 20% of the black patient subclass will have predicted costs greater than $X.

In this manner, the algorithm is not "biased" in terms of reflecting the needs of care (such as colon cancer risk percentages) among minority subclasses versus a reference majority subclass. The adjusted threshold values may be used to qualify patients of different subclasses for interventions or other case management. Although the example described above uses healthcare costs for colon cancer treatment, various implementations may use thresholds that are based on values other than costs, that use other treatment options, that divide subclasses of database entries based on other criteria, etc.

In various implementations, use of automated machine learning models in database systems may introduce technical problems of creating bias in automatically generated claim prediction outputs of the machine learning models. Example computer systems (such as those described herein) may provide a technical solution to the bias introduced by artificial intelligence systems by automatically correcting the bias introduced by the machine learning models.

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. In the written description and claims, one or more steps within a method may be executed in a different order (or concurrently) without altering the principles of the present disclosure. Similarly, one or more instructions stored in a non-transitory computer-readable medium may be executed in different order (or concurrently) without altering the principles of the present disclosure. Unless indicated otherwise, numbering or other labeling of instructions or method steps is done for convenient reference, not to indicate a fixed order.

Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements.

The phrase "at least one of A, B, and C" should be construed to mean a logical (A OR B OR C), using a non-exclusive logical OR, and should not be construed to mean "at least one of A, at least one of B, and at least one of C." The term "set" does not necessarily exclude the empty set. The term "non-empty set" may be used to indicate exclusion of the empty set. The term "subset" does not necessarily require a proper subset. In other words, a first subset of a first set may be coextensive with (equal to) the first set.

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are IEEE Standard 802.15.4 (including the ZIGBEE standard from the ZigBee Alliance) and, from the Bluetooth Special Interest Group (SIG), the BLUETOOTH wireless networking standard (including Core Specification versions 3.0, 4.0, 4.1, 4.2, 5.0, and 5.1 from the Bluetooth SIG).

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module. For example, the client module may include a native or web application executing on a client device and in network communication with the server module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. Such apparatuses and methods may be described as computerized apparatuses and computerized methods. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A computer system comprising:
memory hardware configured to store a machine learning model, historical feature vector inputs, and processor-executable instructions, wherein the historical feature vector inputs include historical claim data structures specific to multiple patient entities; and
processor hardware configured to execute the instructions, wherein the instructions include:
training the machine learning model with the historical feature vector inputs to generate a claim prediction output, by:
separating portions of the historical feature vector inputs into structured training data and structured test data, the structured training data and the structured test data including historical medical claim data structures including patient demographic data, procedure data, class data, provider data and employer data combined in to multiple historical feature vectors for supplying as input to the machine learning model;
training the machine learning model using the structured training data, wherein the machine learning model includes a recurrent neural-network based model including multiple neurons arranged in at least one input layer, at least one hidden layer and at least one output layer, with each connection between neurons in adjacent layers assigned a weight which is changed during training of the recurrent neural-network based model;
testing the trained machine learning model using the structured test data;
evaluating results of testing the trained machine learning model;
adjusting parameters of the machine learning model according to the results of testing the trained machine learning model; and
saving the machine learning model for use in generating claim prediction outputs, in response to a determination that accuracy of the evaluated results is greater than or equal to a specified accuracy threshold;
obtaining data corresponding to a set of multiple patient entities;
for each patient entity in the set of multiple patient entities:
obtaining structured claim data specific to the patient entity and structured demographic data specific to the patient entity;
generating a feature vector input according to the structured claim data;
processing, by the machine learning model, the feature vector input to generate the claim prediction output;
storing the claim prediction output as a predicted future claim value specific to the patient entity; and
assigning the patient entity to a first entity subset or to a second entity subset according to the structured demographic data specific to the patient entity, wherein patient entities belonging to the first entity subset have at least one demographic characteristic that differs from patient entities belonging to the second entity subset;
obtaining a specified predicted healthcare cost threshold output value for entity intervention scheduling or entity case management;
determining a first proportion of patient entities within the first entity subset that have a predicted future claim value exceeding the specified predicted healthcare cost threshold output value;
determining an adjusted predicted healthcare cost threshold output value for the second entity subset according to the first proportion, such that a second proportion of patient entities within the second entity subset that have a predicted future claim value exceeding the adjusted predicted healthcare cost threshold output value is equal to the first proportion;
obtaining an event incidence rate of one or more specified treatments for patient entities of the first entity subset;
obtaining the event incidence rate of the one or more specified treatments for patient entities of the second entity subset;
modifying the adjusted threshold output value according to a ratio of the event incident rates for the first entity subset and the second entity subset;
for each entity in the first entity subset:
determining a predicted future claim value of the entity in the first entity subset; and
in response to the determined predicted future claim value of the entity in the first entity subset exceeding the specified predicted healthcare cost threshold output value, selectively populating a schedule entry for the entity in the first entity subset; and
for each entity in the second entity subset:
determining a predicted future claim value of the entity in the second entity subset; and
in response to the determined predicted future claim value of the entity in the second entity subset exceeding the adjusted predicted healthcare cost threshold output value, selectively populating a schedule entry for the entity in the second entity subset.

2. The system of claim 1 wherein training the machine learning model further includes at least one of training a generalized linear machine learning model and training a decision tree machine learning model.

3. The system of claim 1 wherein selectively populating a schedule entry includes automatically scheduling at least one of a text message intervention, an email intervention, an automated phone call intervention, and a live phone call intervention.

4. The system of claim 1 wherein generating the feature vector input includes generating the feature vector input according to at least one of structured medical history data specific to the patient entity, structured body mass index (BMI) data specific to the patient entity, structured nutrition data specific to the patient entity, the structured demographic data, structured procedure data, structured class data, structured provider data, and structured employer data.

5. The system of claim 1 wherein obtaining the specified threshold output value includes obtaining at least one of an entity treatment amount cutoff value and a specified percentage range cutoff value.

6. The system of claim 1 wherein the instructions further include:
receiving a target demographic group input from a user device; and
defining at least the second entity subset according to the target demographic group input.

7. The system of claim 1 wherein the instructions further include, for each patient entity in the second entity subset:

initiating entity case management for the entity in response to the determined predicted future claim value of the entity in the second entity subset exceeding the adjusted threshold output value.

8. A computerized method of automated bias correction for computer systems, the method comprising:
training a machine learning model with historical feature vector inputs to generate a claim prediction output, wherein the historical feature vector inputs include historical claim data structures specific to multiple patient entities, by:
separating portions of the historical feature vector inputs into structured training data and structured test data, the structured training data and the structured test data including historical medical claim data structures including patient demographic data, procedure data, class data, provider data and employer data combined in to multiple historical feature vectors for supplying as input to the machine learning model;
training the machine learning model using the structured training data, wherein the machine learning model includes a recurrent neural-network based model including multiple neurons arranged in at least one input layer, at least one hidden layer and at least one output layer, with each connection between neurons in adjacent layers assigned a weight which is changed during training of the recurrent neural-network based model;
testing the trained machine learning model using the structured test data;
evaluating results of testing the trained machine learning model;
adjusting parameters of the machine learning model according to the results of testing the trained machine learning model; and
saving the machine learning model for use in generating claim prediction outputs, in response to a determination that accuracy of the evaluated results is greater than or equal to a specified accuracy threshold;
obtaining data corresponding to a set of multiple patient entities;
for each patient entity in the set of multiple patient entities:
obtaining structured claim data specific to the patient entity and structured demographic data specific to the patient entity;
generating a feature vector input according to the structured claim data;
processing, by the machine learning model, the feature vector input to generate the claim prediction output;
storing the claim prediction output as a predicted future claim value specific to the patient entity; and
assigning the patient entity to a first entity subset or to a second entity subset according to the structured demographic data specific to the patient entity, wherein patient entities belonging to the first entity subset have at least one demographic characteristic that differs from patient entities belonging to the second entity subset;

obtaining a specified predicted healthcare cost threshold output value for entity intervention scheduling or entity case management;
determining a first proportion of patient entities within the first entity subset that have a predicted future claim value exceeding the specified predicted healthcare cost threshold output value;
determining an adjusted predicted healthcare cost threshold output value for the second entity subset according to the first proportion, such that a second proportion of patient entities within the second entity subset that have a predicted future claim value exceeding the adjusted predicted healthcare cost threshold output value is equal to the first proportion;
obtaining an event incidence rate of one or more specified treatments for patient entities of the first entity subset;
obtaining the event incidence rate of the one or more specified treatments for patient entities of the second entity subset;
modifying the adjusted threshold output value according to a ratio of the event incident rates for the first entity subset and the second entity subset;
for each entity in the first entity subset:
determining a predicted future claim value of the entity in the first entity subset; and
in response to the determined predicted future claim value of the entity in the first entity subset exceeding the specified predicted healthcare cost threshold output value, selectively populating a schedule entry for the entity in the first entity subset; and
for each entity in the second entity subset:
determining a predicted future claim value of the entity in the second entity subset; and
in response to the determined predicted future claim value of the entity in the second entity subset exceeding the adjusted predicted healthcare cost threshold output value, selectively populating a schedule entry for the entity in the second entity subset.

9. The method of claim 8 wherein selectively populating a schedule entry includes automatically scheduling at least one of a text message intervention, an email intervention, an automated phone call intervention, and a live phone call intervention.

10. The method of claim 8 wherein generating the feature vector input includes generating the feature vector input according to at least one of structured medical history data specific to the patient entity, structured body mass index (BMI) data specific to the patient entity, structured nutrition data specific to the patient entity, the structured demographic data, structured procedure data, structured class data, structured provider data, and structured employer data.

11. The method of claim 8 wherein obtaining the specified threshold output value includes obtaining at least one of an entity treatment amount cutoff value and a specified percentage range cutoff value.

12. The method of claim 8 further comprising:
receiving a target demographic group input from a user device; and
defining at least the second entity subset according to the target demographic group input.

* * * * *